US00PP36160P2

(12) United States Plant Patent
Heuger

(10) Patent No.: US PP36,160 P2
(45) Date of Patent: Sep. 24, 2024

(54) ***HELLEBORUS* PLANT NAMED 'HON 1610'**

(50) Latin Name: ***Helleborus* x *hybridus* X *Helleborus niger***
Varietal Denomination: HON 1610

(71) Applicant: Josef Heuger, Glandorf (DE)

(72) Inventor: Josef Heuger, Glandorf (DE)

( * ) Notice: Subject to any disclaimer, the term of this patent is extended or adjusted under 35 U.S.C. 154(b) by 0 days.

(21) Appl. No.: 18/389,569

(22) Filed: Nov. 14, 2023

(51) Int. Cl.
*A01H 5/02* (2018.01)
*A01H 6/72* (2018.01)

(52) U.S. Cl.
USPC ..... Plt./439
CPC ..... *A01H 6/72* (2018.05)

(58) Field of Classification Search
USPC ..... Plt./439
CPC ..... A01H 6/72; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Helleborus* plant named 'HON 1610', characterized by its upright to somewhat outwardly spreading and mounded plant habit; moderately vigorous growth habit; dark green-colored leaflets with lighter green-colored venation; freely flowering habit; purplish pink-colored flowers; and good garden performance.

1 Drawing Sheet

Figure 1:
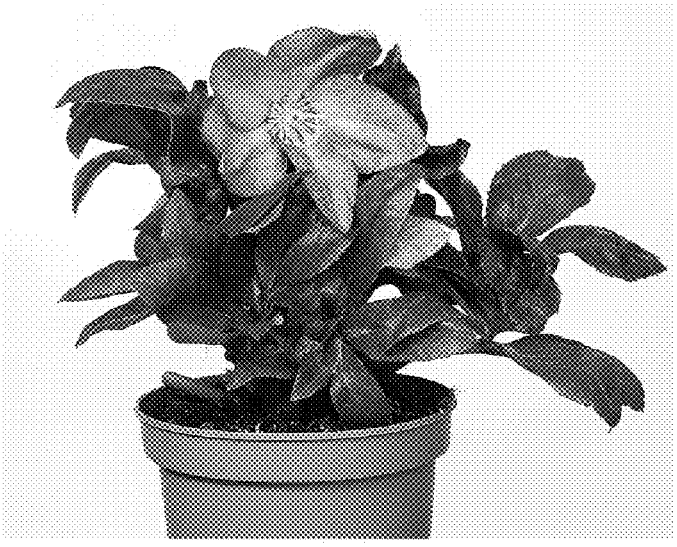

Botanical designation: *Helleborus* x *hybridus* X *Helleborus niger.*
Cultivar denomination: 'HON 1610'.

CROSS-REFERENCED TO CLOSELY-RELATED APPLICATIONS

Title: *Helleborus* Plant Named 'HON 1612'
Inventor/Applicant: Josef Heuger
Filed: Concurrently with the instant application

STATEMENT REGARDING PRIOR DISCLOSURES BY INVENTOR/APPLICANT

An European Community Plant Breeder's Rights application for the instant plant was filed by the Inventor/Applicant, Mr. Josef Heuger of Glandorf, Germany, on Dec. 1, 2022, application number 2022/2786. Foreign priority is not claimed to this application.

The Inventor/Applicant asserts that no publications nor advertisements relating to sales, offers for sale or public distribution occurred more than one year prior to the effective filing date of this application. Any information about the claimed plant would have been obtained from a direct or indirect disclosure from the Inventor or Applicant. Inventor/Applicant claims a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Helleborus* plant, botanically known as *Helleborus* x *hybridus* X *Helleborus niger* and hereinafter referred to by the name 'HON 1610'.

The new *Helleborus* plant is a product of a planned breeding program conducted by the Inventor in Glandorf, Germany. The objective of the breeding program was to create new uniform *Helleborus* plants with unique and attractive plant habit, leaf and flower coloration and tolerance to biotic and abiotic stresses.

The new *Helleborus* plant originated from a cross-pollination conducted by the Inventor in Glandorf, Germany in December, 2013 of a proprietary selection of *Helleborus* x *hybridus* identified as code number O1689, not patented, as the female, or seed, parent and a proprietary selection of *Helleborus* x *hybridus* identified as code number O1412, not patented, as the male, or pollen, parent. The new *Helleborus* plant was discovered and selected by the Inventor as a single flowering plant from within the progeny of the stated cross-pollination grown in a controlled greenhouse environment in Glandorf, Germany in December, 2015.

Asexual reproduction of the new *Helleborus* plant by in vitro axillary meristem culture in a controlled environment in Glandorf, Germany since April, 2016 has shown that the unique features of this new *Helleborus* plant are stable and reproduced true to type in successive generations.

SUMMARY OF THE INVENTION

Plants of the new *Helleborus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'HON 1610'. These characteristics in combination distinguish 'HON 1610' as a new and distinct *Helleborus* plant:

1. Upright to somewhat outwardly spreading and mounded plant habit.
2. Moderately vigorous growth habit.
3. Dark green-colored leaflets with lighter green-colored venation.
4. Freely flowering habit.
5. Purplish pink-colored flowers.
6. Good garden performance.

Plants of the new *Helleborus* differ from plants of the female parent selection in the following characteristics:

1. Plants of the new *Helleborus* are more vigorous than and not as compact as plants of the female parent selection.
2. Flowers of plants of the new *Helleborus* are purplish pink in color whereas flowers of plants of the female parent selection are white in color.

Plants of the new *Helleborus* differ from plants of the male parent selection in the following characteristics:

1. Leaflets of plants of the new *Helleborus* are darker green in color than leaflets of plants of the male parent selection.
2. Flowers of plants of the new *Helleborus* are purplish pink in color whereas flowers of plants of the male parent selection are red in color.

Plants of the new *Helleborus* can be compared to plants of *Helleborus* x *hybridus* X *Helleborus niger* 'HON 1612', disclosed in a U.S. Plant Patent application filed concurrently. In side-by-side comparisons, plants of the new *Helleborus* differ primarily from plants of 'HON 1612' in flower color as plants of the new *Helleborus* have purplish pink-colored flowers whereas plants of 'HON 1612' have purplish red-colored flowers.

Plants of the new *Helleborus* can also be compared to plants of *Helleborus orientalis* 'HLR 180', disclosed in U.S. Plant Pat. No. 22,020. In side-by-side comparisons, plants of the new *Helleborus* differ primarily from plants of 'HLR 180' in flower color as plants of the new *Helleborus* have purplish pink-colored flowers whereas plants of 'HLR 180' have white-colored flowers with red purple-colored spots.

BRIEF DESCRIPTION OF THE PHOTOGRAPHS

The accompanying colored photographs illustrate the overall appearance of the new *Helleborus* plant showing the colors as true as it is reasonably possible to obtain in colored reproductions of this type. Colors in the photographs may differ slightly from the color values cited in the detailed botanical description which accurately describe the colors of the new *Helleborus* plant.

The photograph at the top of the sheet (FIG. 1) is a side perspective view of a typical flowering plant of 'HON 1610' grown in a container.

Figure 2:
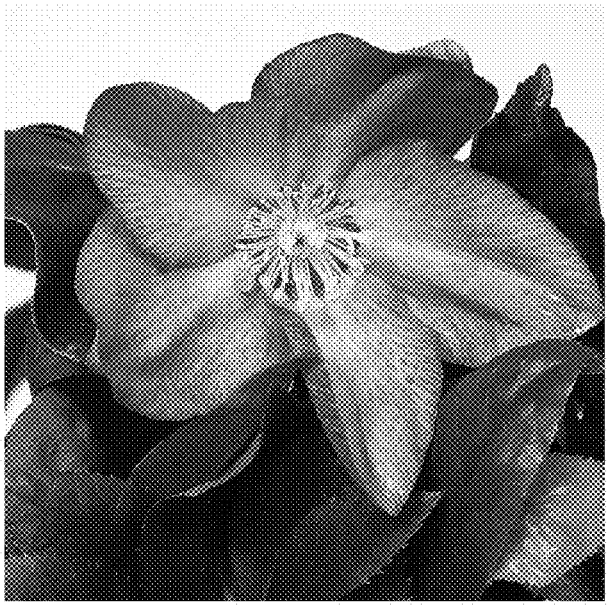

The photograph at the bottom of the sheet (FIG. 2) is a close-up view of a typical flowering plant of 'HON 1610'.

DETAILED BOTANICAL DESCRIPTION

The aforementioned photographs and following observations, measurements and values describe plants grown during the late autumn and early winter in 13-cm containers in a glass-covered greenhouse in Glandorf, Germany and under cultural practices typical of commercial *Helleborus* production. During the production of the plants, day temperatures ranged from 12 C to 32 C and night temperatures ranged from 5 C to 12 C. Plants were 48 weeks old when the photographs were taken and 14 months old when the description was taken. In the following description, color references are made to The Royal Horticultural Society Colour Chart, 2015 Edition, except where general terms of ordinary dictionary significance are used.

Botanical classification: *Helleborus* x *hybridus* X *Helleborus* x *hybridus* 'HON 1610'.

Parentage:

*Female, or seed, parent*.—Proprietary selection of *Helleborus* x *hybridus* identified as code number O1689, not patented.

*Male, or pollen, parent*.—Proprietary selection of *Helleborus niger* identified as code number O1412, not patented.

Propagation:

*Type*.—In vitro axillary meristem culture.

*Time to initiate roots, winter*.—About 55 days at temperatures about 12 C.

*Time to produce a rooted young plant, winter*.—About 170 days at temperatures ranging from about 4 C to 15 C.

*Root description*.—Thick to thin, fleshy; typically white to brownish in color, actual color of the roots is dependent on substrate composition, water quality, fertilizer type and formulation, substrate temperature and physiological age of roots.

*Rooting habit*.—Low branching; sparse.

Plant description:

*Plant and growth habit*.—Herbaceous perennial; upright to somewhat outwardly spreading and mounding plant habit with flowers held within to slightly above the foliar plane; plant shape, roughly flattened globular; moderately vigorous growth habit and slow to moderate growth rate.

*Plant height, soil level to top of foliar plane*.—About 19.6 cm.

*Plant height, soil level to top of flowers*.—About 20.5 cm.

*Plant diameter* (*area of spread*).—About 31.7 cm.

Leaf description:

*Arrangement*.—Leaves arranged in a basal rosette; leaves palmately compound with typically five to seven leaflets per leaf.

*Leaf length*.—About 15.5 cm.

*Leaf width*.—About 16.4 cm.

*Leaflet length*.—About 9.4 cm.

*Leaflet width*.—About 5.4 cm.

*Leaf shape*.—Palmate; roughly reniform in outline.

*Leaflet shape*.—Ovate to elliptic.

*Leaflet apex*.—Acute.

*Leaflet base*.—Attenuate.

*Leaflet margin*.—Serrate; slightly coarsely undulate.

*Leaflet texture and luster, upper surface*.—Smooth, glabrous; moderately coriaceous and tough; moderately glossy.

*Leaflet texture and luster, lower surface*.—Smooth, glabrous; moderately coriaceous and tough; slightly glossy.

*Leaflet venation pattern*.—Pinnate and reticulate.

*Leaflet color*.—Developing leaflets, upper surface: Close to 143A; at the base, tinged with close to 183A and 183B. Developing leaflets, lower surface: Close to a blend of 144A and 147B; venation, close to 176A. Fully developed leaflets, upper surface: Slightly darker than a blend of 139A and 147A; towards the base, close to 200B; venation, close to 144C. Fully developed leaflets, lower surface: Close to 147B; venation, close to 146B and tinged with close to 178A.

*Petioles*.—Length: About 12.5 cm. Diameter: About 5.5 mm by 7 mm. Strength: Strong. Texture and luster, upper and lower surfaces: Smooth, glabrous;

slightly glossy. Color, upper surface: Close to 144A; sparsely to moderately covered with fine dots, close to 200A to 200B; proximally, heavily covered with fine dots, close to 187B. Color, lower surface: Close to 144A to 144B; moderately to heavily covered with fine dots, close to N186C; proximally, heavily covered with fine dots, close to 187B to 187C.

Flower description:

*Flower shape and habit*.—Single rotate bowl-shaped flowers arranged in panicles; freely flowering habit with about two to three flowers per inflorescence and about 13 flowers and flower buds per plant; flowers face mostly outwardly to slightly nodding.

*Fragrance*.—None detected.

*Natural flowering season*.—Plants begin flowering about ten months after planting; plants flower naturally from late autumn into the winter in Germany.

*Flower longevity on the plant*.—About ten days; sepals persistent, other flower parts are not persistent.

*Flower buds*.—Length: About 2.9 cm. Diameter: About 1.2 cm. Shape: Oblong. Texture and luster: Smooth, glabrous; matte. Color: Close to a blend of 145C and 150D; upper surface, flushed with close to 182D and distally, tinged with close to 187B to 187C.

*Inflorescence height* (*including peduncle*).—About 19.1 cm.

*Inflorescence diameter*.—About 14 cm.

*Flower diameter*.—About 9.8 cm.

*Flower depth*.—About 4.6 cm.

*Petals*.—All petals are transformed into nectaries.

*Sepals*.—Quantity and arrangement: About five, arranged in a single whorl. Length: About 5.9 cm. Width: About 4.6 cm. Shape: Broadly ovate; slightly concave. Apex: Broadly and bluntly acute. Base: Broadly attenuate to cuneate. Margin: Entire; coarsely undulate. Texture and luster, upper surface: Smooth, glabrous; matte. Texture and luster, lower surface: Smooth, glabrous; slightly glossy. Color: When opening, upper surface: Close to 76D; towards the margins and apex, strongly flushed with close to 186A and 186B. When opening, lower surface: Close to 76D and strongly flushed with close to 64C; towards the margins and apex, strongly flushed with close to 59A, 59B, 186A and 186B. Fully opened, upper surface: Close to 70C; towards the margins and apex, close to 186B; apex occasionally tinged with close to 146B and 146C; at the base, close to 145B; venation, close to 75C; color does not change with subsequent development. Fully opened, lower surface: Close to 186A flushed with close to 186C; venation, similar to lamina colors; color does not change with subsequent development.

*Flower bracts*.—Quantity per flower: Typically one. Length: About 10.9 cm. Width: About 7.9 cm. Shape: Ovate to broadly obovate. Apex: Acute to two or three-parted. Base: Truncate to cuneate. Margin: Proximally, entire, and distally, serrate; coarsely undulate. Color, upper surface: Close to a blend of NN137A and 139A; towards the base, close to 147D; midvein, occasionally tinged with close to 187B. Color, lower surface: Close to 147B; midvein, close to 183B to 183C.

*Peduncles*.—Length: About 11.4 cm. Diameter: About 7 mm to 8 mm. Aspect: About 15 degrees from vertical. Strength: Strong. Texture and luster: Smooth, glabrous; moderately glossy. Color: Close to 146D; moderately to heavily covered with fine dots, close to 187C.

*Pedicels*.—Length: About 5.1 cm. Diameter: About 3 mm. Aspect: About 20 degrees from peduncle axis. Strength: Moderately strong. Texture and luster: Smooth, glabrous; slightly glossy. Color: Close to 146D; moderately covered with fine dots, close to 187D.

*Reproductive organs*.—Stamens: Quantity per flower: About 100. Filament length: About 1.5 cm. Filament color: Close to 155B. Anther shape: Double and broadly reniform; basifixed. Anther size: About 1.75 mm by 3 mm. Anther color: Close to 154C. Pollen amount: Sparse to moderate. Pollen color: Close to 4D to lighter than 4D. Pistils: Quantity per flower: About four. Pistil length: About 7 mm. Stigma diameter: About 0.3 mm. Stigma shape: Club-shaped. Stigma color: Close to 156D. Style length: About 6.5 mm. Style color: Close to 64B. Ovary color: Close to 150C. Nectaries (transformed petals): Quantity per flower: About 17 to 19. Length: About 1.1 cm. Diameter: About 4 mm. Shape: Tubular, flattened; apices, obtuse. Texture and luster, inner and outer surfaces: Smooth, glabrous; slightly glossy. Color, immature, inner and outer surfaces: Close to 144A; distally, close to 146D; at the base, close to 145B. Color, mature, inner and outer surfaces: Close to N144A; distally, close to 151B and strongly flushed with close to 183D; venation, similar to lamina colors; with subsequent development, color becoming closer to 151B, distally, strongly flushed with close to 178B and at the base, close to 152C.

*Seeds and fruits*.—To date, seed and fruit development have not been observed on plants of the new *Helleborus*.

Garden performance: Plants of the new *Helleborus* have been observed to have good garden performance and to tolerate rain, wind, high temperatures about 35 C and to be suitable for USDA Hardiness Zones 5 through 9.

Pathogen & pest resistance: To date, plants of the new *Helleborus* have not been observed to be resistant to pathogens and pests common to *Helleborus* plants.

It is claimed:

1. A new and distinct *Helleborus* plant named 'HON 1610' as illustrated and described.

* * * * *